US012721883B2

(12) United States Patent
Ivachtchenko et al.

(10) Patent No.: US 12,721,883 B2
(45) Date of Patent: Sep. 1, 2026

(54) ANTIVIRAL AGENT FOR COMBINED THERAPY OF COVID-19 (SARS-CoV-2)

(71) Applicants: Alexandre Vasilievich Ivachtchenko, Hallandale, FL (US); Nikolay Filippovich Savchuk, Rancho Santa Fe, CA (US); Alena Alexandrovna Ivachtchenko, Hallandale, FL (US); Vladimir Grigorievich Loginov, Moscow (RU); Mikhail Topr, New York, NY (US); Andrey Alexandrovich Ivashchenko, Moscow (RU)

(72) Inventors: Alexandre Vasilievich Ivachtchenko, Hallandale, FL (US); Nikolay Filippovich Savchuk, Rancho Santa Fe, CA (US); Alena Alexandrovna Ivachtchenko, Hallandale, FL (US); Vladimir Grigorievich Loginov, Moscow (RU); Mikhail Topr, New York, NY (US); Andrey Alexandrovich Ivashchenko, Moscow (RU)

( * ) Notice: Subject to any disclaimer, the term of this patent is extended or adjusted under 35 U.S.C. 154(b) by 714 days.

(21) Appl. No.: 18/041,926

(22) PCT Filed: Dec. 17, 2020

(86) PCT No.: PCT/RU2020/000727

§ 371 (c)(1),
(2) Date: Feb. 16, 2023

(87) PCT Pub. No.: WO2022/039619

PCT Pub. Date: Feb. 24, 2022

(65) Prior Publication Data

US 2023/0372458 A1 Nov. 23, 2023

(30) Foreign Application Priority Data

Aug. 21, 2020 (RU) ........................... RU2020127969
Aug. 21, 2020 (RU) ........................... RU2020127971
Aug. 21, 2020 (RU) ........................... RU2020127975

(51) Int. Cl.
*A61P 31/14* (2006.01)
*A61K 31/4965* (2006.01)
*A61K 38/57* (2006.01)

(52) U.S. Cl.
CPC .......... *A61K 38/57* (2013.01); *A61K 31/4965* (2013.01); *A61P 31/14* (2018.01)

(58) Field of Classification Search
CPC ...... A61K 38/57; A61K 31/4965; A61P 31/14
See application file for complete search history.

(56) References Cited

U.S. PATENT DOCUMENTS 10,729,735 B1 8/2020 Newman et al.

FOREIGN PATENT DOCUMENTS

| | | | | |
|---|---|---|---|---|
| RU | 2571687 C2 | | 12/2015 | |
| RU | 2711080 C2 | | 1/2017 | |
| RU | 2661028 C2 | | 7/2018 | |
| RU | 2730998 C2 | | 8/2020 | |
| RU | 2731908 C2 | | 9/2020 | |
| RU | 2733392 C1 | | 10/2020 | |
| RU | 2742116 C1 | * | 2/2021 | ............. A61P 31/14 |

OTHER PUBLICATIONS

Kashchenko et al (Year: 2021).*
Bojkova_et_al_Cells_2020 (Year: 2020).*
Vanassche_et_al_Trials_2020_vol. 21 (Year: 2020).*
Tedeschi_et_al_2020 (Year: 2020).*
Solun_2020 (Year: 2020).*
Choudhary_et_al_Frontiers_in_Immunology_published_Jul. 10, 2020 (Year: 2020).*
Machine Translation_of RU_2742116C1 (Year: 2021).*
Ivachtchenko et al ("Effect of Aprotinin and Avifavir . . . " Viruses vol. 13 2021 (Year: 2021).*
Joshi_et_al_Int_J_Infect_Dis_Oct. 30, 2020 (Year: 2020).*
Aguila et al, "Repurposed GI Drugs in the Treatment of COVID-19", Published Online (Jun. 2020), 2 pgs.
Doi et al, "Nafamostat mesylate treatment in combination with favipiravir for patients critically ill with Covid-19: a case series", Critical Care (2020), vol. 24, No. 392, pp. 1-4.
Tallarida R., "Quantitative Methods for Assessing Drug Synergism", Genes & Cancer (Nov. 2011), vol. 2, No. 11, pp. 1003-1008.
Uddin et al., "SARS-CoV-2/COVID-19: Viral Genomics, Epidemiology, Vaccines, and Therapeutic Interventions", Viruses (2020), vol. 12, No. 526, pp. 1-18.

(Continued)

*Primary Examiner* — Catherine S Hibbert
(74) *Attorney, Agent, or Firm* — Paul D. Strain, Esq.; Strain & Strain PLLC

(57) ABSTRACT

This invention relates to a novel anti-coronavirus agent for COVID-19 (SARS-CoV-2) combination therapy. The agent comprises, in a therapeutically effective amount and ratio, aprotinin (APR) or a medicinal drug based thereon and a SARS-CoV-2 replication inhibitor. The aprotinin-based medicinal drug is preferably selected from the group consisting of Aprotex, Vero-Narcap, Ingitril, Contrykal, Kontrisel, Trasilol®, Ingiprol, Aprotimbin, Gordox®, Contriven, Trascolan, or Aerus. For SARS-CoV-2 replication inhibitor one can use favipiravir (FPV) or Remdesivir (RMD), or a medicinal drug based thereon. The favipiravir-based medicinal drug is preferably selected from the group consisting of Avigan, Favilavir, Avifavir, Coronavir, or Fabiflu. Further, the invention relates to a combination method to treat COVID-19 (SARS-CoV-2) by administering said anti-coronavirus agent to a patient with COVID-19.

The use of the novel anti-coronavirus agent in COVID-19 (SARS-CoV-2) therapy leads to a new, synergistic effect and allows one to significantly reduce the duration of treatment and mitigate the risk of undesirable side effects.

15 Claims, No Drawings

(56) References Cited

OTHER PUBLICATIONS

Boikova D., SARS-CoV-2 and SARS-CoV differ in their cell tropism and drug sensitivity profiles, bioRxiv, Apr. 2020, pp. 1-28.

Doi K, Nafamostat mesylate treatment in combination with favipiravir for patients critically ill with Covid-19: a case series , Critical Care, Mar. 7, 2020, vol. 24, pp. 1-4.

Metodicheskie rekomendatsii po diagnostike, lecheniu i profilaktike blizhnevostochnogo respiratornogo sindroma bbuslovlennogo koronav 1arusnoi infektsiei (MERS-Cov), Sankt-Peterburg, 2014, pp. 1-38.

Munir M.A. et al., The Efficacy and Safety of Antivirus Drugs for COVID-19: A Systematic Review, Sys. Rev. Pharm., Aug. 15, 2020, vol. 11, pp. 162-166.

* cited by examiner

ANTIVIRAL AGENT FOR COMBINED THERAPY OF COVID-19 (SARS-CoV-2)

This invention relates to a novel anti-coronavirus agent for COVID-19 (SARS-CoV-2) combination therapy and method of prevention and treatment of COVID-19.

A sudden outbreak of the new coronavirus (later named SARS-CoV-2) in Wuhan, China, in 2019, which quickly turned into a global pandemic, marked the third introduction of a virulent coronavirus into human society, affecting not only the health system, but also the global economy. As of the morning of August 19, the total number of coronavirus infected worldwide exceeded 22.05 million people in 188 countries, with 14.1 million people recovered and 779,557 died.

The SARS-CoV-2 coronavirus belongs to a group of so-called RNA viruses characterized by a high mutation rate in the dissemination period. Despite the fact that SARS-CoV-2 has a relatively low mutation rate, there have appeared early reports of a new coronavirus mutation with different immune characteristics and virulence.

Given that SARS-CoV-2 poses a serious threat to the world's public health and economy, it seems appropriate to search for novel potent anti-coronavirus drugs.

Effective approaches to prevention and treatment of SARS-CoV-2 (COVID-19) and epidemiological control are still extremely scarce. An intensive search for therapeutic agents for the prevention and treatment of SARS-CoV-2 (COVID-19) is underway worldwide. To this end, the World Health Organization and national ministries of health issue temporary, constantly updated guidelines for the prevention, diagnosis and treatment of coronavirus infection using existing therapeutic agents previously intended for other viral infections (influenza, AIDS, Ebola, etc.).

Among the first drugs repurposed to fight COVID-19 were SARS-CoV-2 replication inhibitors Favipiravir (FVP) and Remdesivir (RMD) as well as the SARS-CoV-2 cell entry inhibitor Aprotinin (APR) [A. Azimi.TMPRSS2 inhibitors, Bromhexine, Aprotinin, Camostat and Nafamostat as potential treatments for COVID-19]FVP (6-fluoro-3-hydroxy-2-pyrazinecarboxamide, Favipiravir, RN: 259793-96-9 CA) has antiviral activity against COVID-19 and is part of a number of drugs in tablets containing 200 mg of FVP, including:

- AVIGAN® (favipiravir),
- FAVILAVIR® (favipiravir),
- AVIFAVIR® (favipiravir),
- AREPLIVIR® (favipiravir)
- CORONAVIR® (favipiravir), and
- FABIFLU® (favipiravir).

The adult dose for COVID-19 is 1600 mg twice on the first day (hereinafter day 1) followed by 600 mg twice for 2-10 days (hereinafter on days 2-10) for patients weighing <75 kg, 2000 mg twice on day 1 and then 800 mg twice a day on days 2-10 for patients weighing 75-90 kg (inclusive), and 2400 mg twice on day 1 and 1000 mg twice a day on days 2-10 for patients weighing >90 kg. All doses range from 44 mg/kg to 64 mg/kg. The duration of therapy is 10 days or less in case of confirmed elimination of the virus.

RMD (ethylbutyl (2S)-2-(((S)-(((2R,3S,4R,5R)-5-(4-aminopyrrolo(2,1-f)(1,2,4)triazin-7-yl)-5-cyano-3,4-dihydroxyacetophenon-2-yl)methoxy) (phenoxy)phosphoryl)amino)-propanoate, Remdesivir, RN: 1809249-37-3 CA) is used in the treatment of viral infections (COVID-19): for injection (100 mg) as a sterile, preservative-free lyophilized powder in disposable vials. Unopened vials of lyophilized powder can be stored at temperatures below 30° C. (86° F.). The lyophilized RMD powder is dissolved and diluted with 19 ml of sterile water for injection before use and additionally diluted with saline in an infusion bag. RMD is used for injection (5 mg/ml) as a concentrated solution in single-dose vials. Adult dose for COVID-19: a loading dose of 200 mg intravenously once (day 1) and then a maintenance dose of 100 mg intravenously once a day (days 2 to 5 or 10). The duration of therapy involving invasive mechanical ventilation and/or extracorporeal membrane oxygenation (ECMO) is 10 days; when invasive mechanical ventilation and/or ECMO is not required, 5 to 10 days total.

APR (RN: 9087-70-1) is a polypeptide obtained from the lungs of cattle. Aprotinin blocks the kallikrein-kinin system. It inhibits both the total proteolytic activity and the activity of individual proteolytic enzymes. It is a polyvalent inhibitor of proteases (such as plasmin, kininogenases, trypsin, chymotrypsin, kallikrein, including those that activate fibrinolysis). APR reduces the fibrinolytic activity of the blood, inhibits fibrinolysis, has a hemostatic effect in coagulopathies). APR has been used in medical practice for more than 50 years and is recommended for use in doses for intravenous, jet or drip administration from 100,000 to 1,000,000 KIU. Aprotinin activity is expressed in kallikrein inactivating units (KIU). 100,000 KIU corresponds to 14 mg of Aprotinin [A. V. Ovcharenko and O. P. Zhirnov. Antiviral Research 1994, 23, 107-118].

APR is a part of a number of drugs applied as lyophilizates for preparing solutions for intravenous administration, solutions for intravenous and infusion administration, and aerosols for inhalation, including APROTEX® (aprotinin), lyophilizate, 133,000 KIU/vial, excipients (EXCs): lactose, sodium hydroxide; VERO-NARCAP® (aprotinin), lyophilizate, 30000 TIU/vial (1 TIU=1.33 KIU), EXCs: lactose, sodium hydroxide; INGITRIL® (aprotinin), lyophilizate, 10000 TIU/vial; CONTRYKAL® (aprotinin), 10000 TIU, EXC: mannitol //www.vidal.ru/drugs/contrykal_37338sides; KONTRISEL® (aprotinin), lyophilizate, 10000 KIU/vial, EXCs: lactose monohydrate, trisodium citrate for injection, with 2 ml of 0.9% sodium chloride solution as a solvent in ampoules; TRASILOL® (aprotinin), solution for injection, 500,000 KIU/50 ml bottle), EXCs: sodium chloride, sodium hydroxide and/or hydrochloric acid solution (for pH adjustment), water for injection; INGIPROL® (aprotinin) solution for infusions, 10000 KIU/ml, 2 ml ampoule, and lyophilizate for preparation of solution for infusion; APROTIMBIN® (aprotinin), solution for injection, 100,000 KIU and 500,000 KIU, 10 ml ampoules; GORDOX® (aprotinin), solution for injection, 100,000 KIU, 10 ml ampoule, EXCs: 85 mg of sodium chloride, 100 mg of benzyl alcohol, water for injection up to 10 ml; CONTRIVEN® (aprotinin), water for injection, 10000 KIU/ml of aprotinin, 1 ml ampoules, EXCs: sodium chloride, water for injection; TRASCOLAN® (aprotinin), water for injection, 100,000 KIU and 500,000 KIU, 10 ml ampoules; AERUS® (aprotinin), dosed aerosol for inhalation, in a metal (aluminum) cylinder with a capacity of 30 or 20 ml, respectively, with a dosing device (valve), 35000 KIU (350 doses) or 25000 KIU (250 doses), EXCs: 0.045 ml of propellant HFC-134A (1,1,1,2-tetrafluoroethane), 0.000045 ml of peppermint leaf oil, 0.0075 ml of ethanol 96%, 0.0035 ml of glycerol 96%, and purified water (EurPh); one dose of AERUS® (aprotinin) aerosol is 85 KIU, and the recommended daily dose does not exceed 2000 KIU.

The present inventors have surprisingly discovered that the use of an antiviral combination agent comprising a SARS-CoV-2 replication inhibitor and Aprotinin (APR) or a drug based thereon in a therapeutically effective amount and ratio in COVID-19 (SARS-CoV-2) combination therapy considerably increases the efficacy of treatment. In particular, it can significantly speed the treatment and reduce the risk of undesirable side effects.

It is known that for quick use, protection from external factors, as well as increasing the shelf life of combined drugs for the treatment of various diseases, including viral, pharmaceutical kits are used in packaging. This describes a method of using such kits (see, for example, patents RU 2661028 C2 and RU 2571687 C2).

One of the variants of the invention is the use of an antiviral combined agent comprising a replication inhibitor SARS-CoV-2 and aprotinin (APR) or a drug based on it in a therapeutically effective amount and ratio for combination therapy of COVID-19 (SARS-CoV-2) leads to a significant increase in the effectiveness of patient care. In particular, it can significantly shorten the treatment time and reduce the risk of unwanted side effects.

Thus, the subject of the present invention is a specified new combined anti-coronavirus agent and a method for treating patients with COVID-19 (SARS-CoV-2) using said agent.

The use of a new anti-coronavirus agent in combination therapy results in a new and synergistic effect unknown in the art and not obvious to a person skilled in the art.

One of the variants of the present invention is a new pharmaceutical kit for the combination therapy of coronavirus disease COVID-19 (SARS-CoV-2), including:

A. aprotinin (APR) in a therapeutically effective amount in the form of a finished medicinal product or in the form of finished product components suitable for its administration;

B. SARS-CoV-2 replication inhibitor in a therapeutically effective amount in the form of a finished medicinal product or in the form of ready-made drug components suitable for its administration, with a therapeutically effective ratio of APR and replication inhibitor, placed in a package that protects the drugs from external factors, and C. instructions for use.

Thus, the subject of the present invention is the above-mentioned new combination anti-coronavirus agent and method for treating patients with COVID-19 (SARS-CoV-2) using said agent. The subject of the present invention is also a method of using the specified pharmaceutical kit for the combination therapy of coronavirus disease COVID-19 (SARS-CoV-2), which consists in the simultaneous or sequential administration of the components of the kit—Aprotinin (APR) or a finished drug based on it to a patient with COVID-19, and replication inhibitor SARS-CoV-2. in a therapeutically effective amount and ratio.

The use of a new anti-coronavirus agent in combination therapy leads to a new, synergistic effect, unknown in the state of the art and unobvious to one skilled in the art.

Thus, when using the combination agent of this invention, the 2-point median clinical improvement of patients hospitalized with COVID-19, clinical status 4, was achieved for 5 days, i.e. 1.6 times faster than in FVP treatment (8 days) and 2.2 times faster than in APR treatment (11 days), and the median normalization of C-reactive protein concentration (CRP indicates the presence or absence of the body's acute inflammatory process) was achieved for 1 day, i.e. it was 13 times shorter than in FVP treatment and 9 times shorter than in APR treatment (Table 1).

The time for normalization of the CRP index in the patient's blood is drastically reduced indicating the presence of synergy when using a combination agent of this invention.

Listed below are definitions of terms used to describe this invention.

The term "medication" refers to a substance or mixture of substances with established pharmacological activity and is used for preventive or therapeutic purposes.

The term "medicinal drug" refers to a medication in a finished dosage form.

The term "pharmaceutical composition" refers to a composition comprising a medication and at least one additional component selected from the group consisting of pharmaceutically acceptable and pharmacologically compatible fillers, solvents, diluents, carriers, excipients, distributing and receptive agents, delivery agents such as preservatives, stabilizers, fillers, disintegrators, moisteners, emulsifiers, suspending agents, thickeners, sweeteners, flavoring agents, aromatizing agents, antibacterial agents, fungicides, lubricants, and prolonged delivery controllers, the choice and proportions of which depend on the nature and route of administration and dosage. Examples of suitable suspending agents are ethoxylated isostearyl alcohol, polyoxyethylene, sorbitol and sorbitol ether, microcrystalline cellulose, aluminum metahydroxide, bentonite, agar-agar and tragacant, and mixtures thereof. Protection against microorganisms can be provided using various antibacterial and antifungal agents, such as parabens, chlorobutanol, sorbic acid, and the like. Said composition may also include isotonic agents, such as sugar, sodium chloride, and the like. The sustained action of the composition can be achieved using agents that decelerate the absorption of the active ingredient, for example, aluminum monostearate and gelatin. Examples of suitable carriers, solvents, diluents, and delivery agents include water, ethanol, polyalcohols and mixtures thereof, natural oils (such as olive oil), and organic esters (such as ethyl oleate) for injections. Examples of fillers are lactose, milk sugar, sodium citrate, calcium carbonate, calcium phosphate, and the like. Examples of disintegrators and distributors are starch, alginic acid and salts thereof, and silicates. Examples of lubricants are magnesium stearate, sodium lauryl sulfate, talc, and polyethylene glycol of high molecular weight.

The term "inert filler," as used herein, refers to a compound that is used for forming a pharmaceutical composition and is, as a rule, safe, nontoxic, and neither biologically nor otherwise undesirable, and comprises excipients acceptable for veterinary and human pharmaceutical use.

Compounds of this invention may be administered individually, but they will be generally administered in a mixture with one or more pharmaceutically acceptable excipients, diluents, or carriers chosen depending on the contemplated route of drug administration and standard pharmaceutical practice.

The term "therapeutically effective amount," as used herein, refers to an amount of a substance or drug needed for alleviating the symptoms of the disease in the subject. The dose of a substance or drug will meet individual demands in each particular case. Said dose may vary in a wide range depending on numerous factors like the severity of the disease to be treated, the age and the general condition of the patient, other medications used for the patient's treatment, the mode and route of administration, and the experience of the attending doctor.

As a rule, in order to alleviate or eliminate the virus, a higher loading dose is given at the beginning of treatment with a subsequent reduction of the dose to a level sufficient to prevent an infection outburst.

The term "subject" refers to a mammal including, but not limited to, cattle, hogs, sheep, chickens, turkeys, buffalos, lamas, ostriches, dogs, cats, and humans; a human subject is most preferable.

Below is a detailed description of specific embodiments of this invention However, these data will illustrate the present invention without limiting the applicant's claims. Various modifications of the invention are possible within the scope of the stated claims.

The 2-point median clinical improvement of patients hospitalized with COVID-19 and clinical status 4, was achieved for 5 days (Table 1), i.e. 1.6 times faster than in FVP treatment (8.0 days) and 2.2 times faster than in APR treatment (11 days).

One of the important indicators revealing the presence or absence of an acute inflammatory process in the body is the concentration of C-reactive protein (CRP) in the patient's blood. The normal CRP concentration is 5 mg/l, and it does not depend on age or gender [https://sosudinfo.ru/krov/c-reaktivnyj-belok/]. In COVID-19 patients, a significant increase of CRP concentration is observed, which indicates the presence of an acute inflammatory process in the patient's body.

It can be seen from Table 5 that patients treated with FVP had initial CRP=67.5 (45.3-108.6) mg/l, and the median CRP normalization was 8 days (Table 1).

Patients treated with APR had initial CRP=21.5±8.2 mg/l (Table 8), and the median CRP normalization was 11 days (Table 1).

Patients treated with combination agent of this invention had similar initial CRP value=38.7±7.5 mg/l (Table 2), and the median CRP normalization was just 1 day, i.e., when using the combination agent of this invention CRP normalization occurred 8 times and 11 times faster than in treating with FVP and APR, respectively. This indicates that in the treatment of patients with a combination agent of this invention, the suppression of the acute inflammatory process in the patient's body is far more effective than in the treatment with individual components of the combination agent (FVP and APR), i.e. there is a synergy of anti-inflammatory action.

One of the important markers predicting a severe course of COVID-19 is the D-dimer formed during the breakdown of fibrin, a fibrous protein that is the basis of blood clots. An increased concentration of D-dimer is indicative of the formation of small blood clots in the body. A D-dimer test allows one to evaluate 2 factors at once: coagulation (blood clotting) and fibrinolysis (dissolution of blood clots). The marker makes it possible to timely detect an imbalance between them in the case of diseases of the circulatory system (varicose veins, thrombophilia, pulmonary embolism, etc.). A significant increase in D-dimer concentration is a strong predictor of mortality. This indicator is an early and useful marker and must be determined in patients entering dangerous phases of the disease. Normally, the D-dimer should not exceed 250 ng/ml (0.55 μg FEU/ml) [https://aif.ru/health/coronavirus/pokazateli_smerti_uchenye_ob-naruzhili_markery_tyazhelogo_techeniya_covid-19. http://cardiobook.ru/d-dimer/. https://www.diagnos.ru/procedures/analysis/koagulogramma/d-dimer].

The baseline D-dimer concentration value in the blood of patients with COVID-19 admitted to hospital with clinical status 4 was 55.5±142.5 ng/ml (Table 2) and returned to normal just after 5 days of treatment with the combination agent of this invention. SARS-CoV-2 elimination was also rapid (median 3.5 days), and the temperature normalized in one day (Table 1).

According to computer tomography data, on day 14 all patients (100%) treated with a combination agent of this invention showed improvement in lung damage, while for those treated with FVP the figure was 72.7%, with 9.1% of patients having lung damage unchanged and 18.2% of patients showing deterioration of lung damage. For patients treated with APR, this figure was 60.0%, with 40.0% of patients having lung damage unchanged (Table 1).

Consequently, the agent of this invention has demonstrated a high efficacy in the combination therapy of human coronaviral, which considerably exceeded the efficacy of its components.

No serious adverse events were reported during the study. The adverse reactions noted in some cases were mild or moderate in severity and in most cases did not require additional treatment.

TABLE 1

Cure rates of patients hospitalized with COVID-19, clinical status 4, treated with the combination agent of this invention and its components

| Criteria | APR + FPV | FPV | APR |
|---|---|---|---|
| Median clinical improvement, 2 points, days | 5 (5-5) | 8 (6-11) | 11.0 (6-11) |
| Median CRP normalization, days | 1 (1-3) | 13 (13-) | 9 (6-0) |
| Median D-dimer normalization, days | 5 (4-5) | N/T | 4.5 (3-6) |
| Median SARS-CoV-2 elimination, days | 3.5 (3-4) | 4.5 (4-6) | 7.5 (6-9) |
| Median body temperature normalization (<37° C.), days | 1 (1-3) | 3 (2-4) | 3 (2-4) |
| CT on Day 14: | | | |
| Improvement | 10 (100.0%) | 8 (72.7%) | 6 (60.0%) |
| No change | | 1 (9.1%) | 4 (40.0%) |
| Worsening | | 2 (18.2%) | |

The effective amounts of SARS-CoV-2 replication inhibitors and APR administered are listed above and are common for these compounds. The clinical dosage of the agent's components may vary depending on the patient's age, gender, weight, and disease status. The effective ratio of components will be determined by the effective amount of corresponding active ingredient to be administered to the patient.

The agent to be used in the combination therapy of human coronavirus diseases can be a finished dosage form containing APR selected from well-known medications: APRO- TEX® (aprotinin), VERO-NARCAP® (aprotinin), INGITRIL® (aprotinin), CONTRYKAL® (aprotinin), KONTRISEL® (aprotinin), TRASILOL® (aprotinin), INGIPROL® (aprotinin), APROTIMBIN® (aprotinin), GORDOX® (aprotinin), CONTRIVEN® (aprotinin), TRASCOLAN® (aprotinin), or AERUS® (aprotinin).

The SARS-CoV-2 replication inhibitor can be FPV or a finished dosage form containing FPV, such as AVIGAN® (favipiravir), FAVILAVIR® (favipiravir), AVIFAVIR® (favipiravir), AREPLIVIR® (favipiravir), CORONAVIR® (favipiravir), or FABIFLU® (favipiravir).

FPV is administered to the patient orally and APR and RMD, parenterally (for example, intravenously, subcutaneously, intraperitoneally, by inhalation, as a spray or as drops.

For APR, the preferred daily dose depends on the severity of the disease and the route of administration and varies between 500,000 KIU and 1,000,000 KIU.

For FPV, the preferred adult dose, depending on the severity of the disease, is 1200-1600 mg twice on day 1 followed by 400-600 mg twice a day on days 2-10 for patients weighing <75 kg, 2000 mg twice on day 1 followed by 800 mg twice a day on days 2-10 for patients weighing 75-90 kg (inclusive), and 2400 mg twice on day 1 and 1000 mg twice a day on days 2-10 for patients weighing >90 kg. All doses range from 44 mg/kg to 64 mg/kg. The duration of therapy is 10 days or less in case of confirmed elimination of the virus.

For RMD, the preferred adult dose is 200 mg intravenously once on day 1 followed by a maintenance dose of 100 mg intravenously once a day (days 2 to 5 or 10).

The dose size of anti-coronavirus components may vary depending on the severity of the condition to be relieved. It should be understood that for each specific subject, the specific dosage regimen and schedule can be adjusted over time according to the individual's needs and the professional judgment of the person who is treating or following up the patient subjected to combination therapy.

Combination therapy can be sequential, which means treating the patient first with one component and then with another, for example, when each stage of treatment involves a different component of the present invention or both components can be administered simultaneously.

Sequential therapy may involve considerable time between the end of treatment with one component and the start of treatment with the second component. Treatment with both components at the same time can be carried out in one daily dose or in different doses.

More preferable is an agent comprising anti-coronavirus components APR and FPV in a therapeutically effective amount.

For the combination therapy of coronavirus disease, concomitant therapeutic drugs can be used, which may be useful if combined and compatible with the anti-coronavirus agent of this invention.

As concomitant therapeutic drugs according to this invention, analgesics (acetylsalicylic acid, paracetamol), angioprotectors (diosmin), antibacterial drugs for systemic use (Avelox, azithromycin, amoxicillin), amoxicillin in combination with enzyme inhibitors (levofloxacin, Meropenem, Metronidazole, Cefazolin, Ceftriaxone), antihistamines for systemic action, anticoagulants (fraxiparin, enoxaparin), beta-blockers (bisoprolol, metoprolol), calcium channel blockers (amlodipine, tifedipine), vitamins (ascorbic acid, vitamin C), lipid-lowering drugs (rosuvastatin), diuretics (spironolactone, hypothyazide, indapamide, furosemide), immunosuppressants (tocilizumab, etanercept), corticosteroids for systemic use (dexamethasone, methylprednisolone, prednisolone), plasma-substituting and perfusion solutions (glucose, sodium chloride, sterofundin isotonic), drugs for the treatment of diseases associated with impaired acidity (omeprazole), drugs for the treatment of heart diseases (cardiket, nitroglycerin), drugs for the treatment of thyroid diseases (L-thyroxine), drugs for the treatment of obstructive respiratory diseases (fenoterol), drugs that affect the renin-angiotensin system (valsartan, losartan, lorista, enalapril), antiviral drugs for systemic use (lopinavir, ritonavir), antidiarrheal medications (Acipol, diosmectitol, sulfosalazine), antitussive drugs and remedies for the treatment of colds (Ambroxol, acetylcysteine, mucaltin), antitumor hormonal drugs (tamoxifen), other drugs for the treatment of gastrointestinal diseases and metabolic disorders (ademetionine), drugs for the treatment of diabetes (apidra, levemir, metformin, novomix) and others.

This invention is illustrated by, but not limited to, the following examples.

EXAMPLE 1. EFFICACY OF TREATMENT WITH THE COMBINATION AGENT OF THIS INVENTION IN PATIENTS HOSPITALIZED WITH MODERATE COVID-19 AND CLINICAL STATUS 4

The clinical study covered 10 patients hospitalized with moderate COVID-19 and clinical status 4 who received separately intravenous APR and oral FPV. Demographic and other baseline characteristics of patients are presented in table 2.

TABLE 2

Demographic and other baseline characteristics of 10 patients hospitalized with COVID-19 and clinical status 4 and were treated with the combination agent of this invention

| Status | Value |
|---|---|
| Age (years) | 46.7 ± 10.6 |
| 18-44 | 4 (40.0%) |
| 45-59 | 5 (50.0%) |
| ≥60 | 1 (10.0%) |
| Men | 8 (80.0%) |
| Women | 2 (20.0%) |
| Body mass (kg) | 80.7 ± 6 |
| BMI (kg/m$^2$) | 26.4 ± 1.5 |
| Disease duration (days) | 3.4 ± 0.8 |
| ≤7 days | 10 (100.0%) |
| >7 days | 0 (0.0%) |
| SpO2 (%) | 95.0 ± 0.9 |
| ≥95 | 6 (60.0%) |
| <95 | 4 (40.0%) |
| Temperature (° C.) | 38.5 ± 0.4 |
| <37 | 0 (0.0%) |
| 37-38 | 1 (10.0%) |
| >38 | 9 (90.0%) |
| RR (per minute) | 21.8 ± 1 |
| ≤22 | 7 (70.0%) |
| >22 | 3 (30.0%) |
| CRP (mg/l) | 38.7 ± 7.5 |
| Normal | 0 (0.0%) |
| Increased | 7 (70.0%) |
| D-dimer (ng/ml) | 855.5 ± 142.5 |
| Normal | 0 (0.0%) |
| Increased | 10 (100.0%) |

Clinical trials were conducted in a Smolensk clinic, RF, in accordance with the Clinical Trial Protocol.

Basic objective: to evaluate and compare the efficacy of an anti-coronavirus agent (intravenous APR+oral FPV) in patients hospitalized with COVID-19 and clinical status 4 using the following parameters:

Time to elimination of SARS-CoV-2 virus to Day 10;

Time to normalize CRP to Day 10.

Time to normalize D-dimer to Day 10.

Additional objectives: evaluation of the following parameters of drug efficacy and safety in patients hospitalized with COVID-19:

Time to normalization of body temperature (<37° C.);

Dynamics of changes in laboratory parameters on Day 4, Day 5, Day 6, Day 10, and Day 14 relative to the baseline values: total blood count (number of neutrophils, white blood cells, and their ratio, number of platelets), CRP, coagulogram (D-dimer, fibrinogen, Quick's value, INR);

Dynamics of changes in laboratory parameters on Day 4, Day 5, Day 6, Day 10 and Day 14 relative to the baseline values: total blood count (number of neutrophils and white blood cells and their ratio, number of platelets), CRP, coagulogram (D-dimer, fibrinogen, Quick's value, INR);

Frequency of clinical status improvement by 2 points on the ordinal scale of clinical improvement or discharge from the hospital before Day 14;

Frequency of transfer to the intensive care unit (ICU), frequency of non-invasive ventilation (NIV), frequency of artificial lung ventilation (ALV), and mortality;

Frequency of adverse events (AE) and serious adverse events (SAE) of varying severity based on subjective complaints, physical examination, vital signs, laboratory tests, and ECG.

Study Design:

All 10 patients received a combination drug (Table 3). APR was administered intravenously by drop infusion (slowly for 15-20 minutes), depending on the patient's condition, from 500,000 KIU to 1,000,000 KIU once a day for 5 days in addition to FPV in tablets: for patients weighing less than 75 kg and depending on the condition, 1200-1600 mg twice on day 1 followed by 400-600 mg twice a day on days 2-10; for patients weighing from 75 kg to 90 kg (inclusive), 2000 mg twice on day 1 followed by 800 mg 2 times a day on days 2-10; for patients weighing more than 90 kg, 2400 mg twice on day 1 and then 1000 mg 2 times a day on days 2-10 (Table 3).

TABLE 3

Daily doses of the components of the combination agent received by patients treated from COVID-19

| Patient | Age, years | Body height, cm | Body mass, kg | Body mass index, kg/m$^2$ | APR dose (KIU), once a day Day 1-5 | FPV dose (mg), twice a day Day 1 | FPV dose (mg), twice a day Day 2-10 |
|---|---|---|---|---|---|---|---|
| 16-2 | 36 | 181 | 85.3 | 26.04 | 1 000 000 | 2000 | 800 |
| 17-2 | 46 | 182 | 88.5 | 26.72 | 1 000 000 | 2000 | 800 |
| 21-2 | 34 | 172 | 80.2 | 27.2 | 1 000 000 | 2000 | 800 |
| 22-2 | 40 | 175 | 72.1 | 23.6 | 500 000 | 1200 | 400 |
| 23-2 | 59 | 166 | 77.5 | 28.2 | 1 000 000 | 2000 | 800 |
| 25-2 | 35 | 177 | 78.4 | 25 | 1 000 000 | 2000 | 800 |
| 26-2 | 48 | 180 | 86.3 | 26.6 | 1 000 000 | 2000 | 800 |
| 28-2 | 65 | 167 | 81.2 | 29.1 | 1 000 000 | 2000 | 800 |
| 29-2 | 52 | 181 | 85.9 | 26.22 | 1 000 000 | 2000 | 800 |
| 30-2 | 52 | 166 | 71.1 | 25.8 | 1 000 000 | 1600 | 600 |

Depending on the patients' condition and concomitant to COVID-19 diseases they received respective concomitant therapy (Table 4).

TABLE 4

Concomitant therapeutics used to treat patients hospitalized with COVID-19 and clinical status 4 with the combination agent of this invention

| Drug | X[a] | %[b] | Y[c] |
|---|---|---|---|
| Paracetamol | 1 | 9.1 | 1 |
| Azithromycin | 3 | 27.3 | 3 |
| Amoxiclav | 1 | 9.1 | 1 |
| Imipenem and dehydropeptidase inhibitor | 1 | 9.1 | 1 |
| Levofloxacin | 1 | 9.1 | 1 |
| Meropenem | 1 | 9.1 | 1 |
| Sulbactam | 1 | 9.1 | 1 |
| Thiamphenicol | 2 | 18.2 | 2 |
| Cefoperazone | 2 | 18.2 | 2 |
| Ceftriaxone | 1 | 9.1 | 1 |
| Enoxaparin | 4 | 36.4 | 4 |
| Hydroxychloroquine | 1 | 9.1 | 1 |
| Bisoprolol | 1 | 9.1 | 1 |
| Amlodipine | 1 | 9.1 | 1 |
| Ascorbic acid | 2 | 18.2 | 2 |
| Hydrochlorothiazide | 1 | 9.1 | 1 |
| Spironolactone | 1 | 9.1 | 9.1 |
| Tocilizumab | 1 | 9.1 | 9.1 |
| Dexamethasone | 1 | 9.1 | 9.1 |
| Glucose | 1 | 9.1 | 9.1 |
| Sodium chloride | 2 | 18.2 | 3 |
| Omeprazole | 1 | 9.1 | 1 |
| Levothyroxine sodium | 1 | 9.1 | 1 |
| Drotaverine | 1 | 9.1 | 1 |
| Losartan | 1 | 9.1 | 1 |
| Losartan in combination with diuretics | 1 | 9.1 | 1 |
| Pancreatin | 1 | 9.1 | 1 |
| Ambroxol | 1 | 9.1 | 1 |
| Insulin | 1 | 9.1 | 1 |
| Insulin glulisine | 1 | 9.1 | 1 |
| Detemir insulin | 1 | 9.1 | 1 |
| Metronidazole | 1 | 9.1 | 1 |

X and % denote the number and percent of patients experiencing at least one event from this group;
Y is the total number of events in this group.

The cure rates of patients hospitalized with moderate COVID-19, clinical status 4, who were treated with the combination agent of this invention are presented in Table 1.

EXAMPLE 2. EFFICACY OF TREATMENT WITH FAVIPIRAVIR (FPV) APPLIED TO COVID-19 PATIENTS HOSPITALIZED WITH CLINICAL STATUS 4

The clinical study covered 11 patients who received oral FPV. The trials were conducted in a Smolensk clinic, Russia, in accordance with the Clinical Trial Protocol. The trials used identical protocols for all the tests for all patients. Demographic and other baseline characteristics of patients are presented in Table 5.

TABLE 5

Demographic and other baseline characteristics of patients hospitalized with COVID-19 and clinical status 4 treated with favipiravir (FPV)

| Status | Value |
|---|---|
| Age (years) | 57.5 ± 15.9 |
| 18-44 | 2 (18.2%) |
| 45-59 | 5 (45.5%) |
| ≥60 | 4 (36.4%) |
| Men | 3 (27.3%) |
| Women | 8 (72.7%) |
| Body mass (kg) | 84.0 ± 16.8 |
| BMI (kg/m$^2$) | 30.7 ± 5.3 |
| Disease duration (days) | 7.3 ± 3 |
| ≤7 days | 3 (27.3%) |
| >7 days | 8 (72.7%) |
| SpO2 (%) | 93.4 ± 1.8 |
| ≥95 | 3 (27.3%) |
| <95 | 8 (72.7%) |
| Temperature (° C.) | 37.5 ± 0.7 |
| <37 | 2 (18.2%) |
| 37-38 | 7 (63.6%) |
| >38 | 2 (18.2%) |
| RR (per minute) | 20.4 ± 1.5 |
| ≤22 | 10 (90.9%) |
| >22 | 1 (9.1%) |
| CRP (mg/l) | 67.5 (45.3-108.6) |
| Normal | 0 (0.0%) |
| Increased | 11 (100.0%) |

Basic objective: to evaluate the efficacy of favipiravir (FPV) in patients hospitalized with COVID-19 and clinical status 4 using the following parameters:

Time to elimination of SARS-CoV-2 virus to Day 10;

Time to normalize CRP to Day 10.

Additional objectives are the same as in Example 1.

Study Design:

All 11 patients received oral FPV in tablets as follows: patients weighing less than 75 kg, depending on their condition, 1200-1600 mg twice on day 1 followed by 400-600 mg twice a day on days 2-10; patients weighing from 75 kg to 90 kg (inclusive), 2000 mg twice on day 1 followed by 800 mg twice a day on days 2-10; patients weighing more than 90 kg, 2400 mg twice on day 1 followed by 1000 mg twice a day on days 2-10 (Table 6).

TABLE 6

Daily doses of the components of the combination drug received by patients treated from COVID-19 with favipiravir (FPV)

| Patient | Age, years | Body height, cm | Body mass, kg | Body mass index, kg/m$^2$ | FPV dose (mg), twice a day Day 1 | Day 2-10 |
|---|---|---|---|---|---|---|
| 02-001 | 53 | 170 | 120 | 41.52 | 1800 | 800 |
| 02-003 | 49 | 173 | 95 | 31.74 | 1600 | 600 |
| 04-001 | 83 | 158 | 90 | 36.05 | 1600 | 600 |
| 04-007 | 59 | 158 | 83 | 33.25 | 1600 | 600 |
| 05-001 | 60 | 158 | 70 | 28.04 | 1800 | 800 |
| 05-002 | 36 | 176 | 80 | 25.83 | 1800 | 800 |
| 05-003 | 76 | 160 | 82 | 32.03 | 1800 | 800 |
| 05-005 | 56 | 175 | 92 | 30.04 | 1800 | 800 |
| 05-009 | 56 | 158 | 63 | 25.24 | 1600 | 600 |
| 05-011 | 74 | 170 | 90 | 31.14 | 1800 | 800 |
| 05-012 | 31 | 161 | 59 | 22.76 | 1600 | 600 |

Depending on the patients' condition and concomitant to COVID-19 diseases they received respective concomitant therapy (Table 7).

TABLE 7

Concomitant therapeutics received by patients hospitalized with COVID-19 and clinical status 4 who were treated with favipiravir (FPV).

| Drug | X[a] | %[b] | Y[c] |
|---|---|---|---|
| Chronic pancreatitis | 2 | 18.2 | 2 |
| Chronic gastritis | 1 | 9.1 | 1 |
| Pneumonia | 9 | 81.8 | 9 |
| Viral pneumonia | 1 | 9.1 | 1 |
| Hyperlipidemia | 1 | 9.1 | 1 |
| Dyslipidemia | 1 | 9.1 | 1 |
| Obesity | 6 | 54.5 | 6 |
| Type 2 diabetes | 4 | 36.4 | 4 |
| Bronchitis, chronic | 1 | 9.1 | 1 |
| Pain in the back | 1 | 9.1 | 1 |
| Ostearthritis | 1 | 9.1 | 1 |
| Osteochondrosis | 1 | 9.1 | 1 |
| Headache | 1 | 9.1 | 1 |
| Cerebral ischemia | 1 | 9.1 | 1 |
| Glaucoma | 1 | 9.1 | 2 |
| Myopia | 1 | 9.1 | 1 |
| Vertigo | 1 | 9.1 | 1 |
| Cholecystitis | 1 | 9.1 | 1 |
| Chronic kidney disease | 1 | 9.1 | 1 |
| Myocardial ischemia | 3 | 27.3 | 3 |
| Arteriosclerosis | 1 | 9.1 | 1 |
| Varicose veins | 1 | 9.1 | 1 |
| Hypertension | 6 | 54.5 | 6 |
| Deep vein thrombosis | 1 | 9.1 | 1 |
| Phlebitis | 1 | 9.1 | 1 |
| Menopause | 6 | 54.5 | 6 |
| Fracture of thoracic vertebra | 1 | 9.1 | 1 |
| Tendon tear | 1 | 9.1 | 1 |
| Appendectomy | 1 | 9.1 | 1 |
| Hysterectomy | 1 | 9.1 | 1 |
| Vein ligation | 1 | 9.1 | 2 |
| Polypectomy of the stomach | 1 | 9.1 | 1 |
| Retinal laser coagulation | 1 | 9.1 | 2 |
| Cholecystectomy | 1 | 9.1 | 1 |
| Endocrine disorders | 1 | 9.1 | 1 |
| Hypothyroidism | 1 | 9.1 | 1 |

The cure rates of patients hospitalized with COVID-19, clinical status 4, who were treated with favipiravir are presented in Table 1.

EXAMPLE 3. EFFICACY OF TREATMENT WITH APROTININ (APR) APPLIED TO PATIENTS HOSPITALIZED WITH COVID-19 AND CLINICAL STATUS 4

The clinical study covered 10 patients who received IV APR. Demographic and other baseline characteristics of patients are presented in Table 8.

TABLE 8

Demographic and other baseline characteristics of COVID-19 patients hospitalized with clinical status 4 and subjected to treatment with aprotinin (APR)

| Status | Value |
|---|---|
| Age (years) | 44.9 ± 11.2 |
| 18-44 | 4 (40.0%) |
| 45-59 | 6 (60.0%) |
| ≥60 | 0 (0.0%) |
| Men | 3 (30.0%) |
| Women | 7 (70.0%) |
| Body mass (kg) | 74.3 ± 4.7 |
| BMI (kg/m$^2$) | 25.9 ± 1.7 |
| Disease duration (days) | 3.4 ± 1.1 |
| ≤7 days | 10 (100.0%) |
| >7 days | 0 (0.0%) |
| SpO2 (%) | 96.7 ± 1.1 |
| ≥95 | 10 (100%) |
| >95 | 0 (0.0%) |
| Temperature (° C.) | 38.3 ± 0.1 |
| <37 | 0 (0.0%) |
| 37-38 | 0 (0.0%) |
| >38 | 10 (100%) |
| RR (per minute) | 21.4 ± 1.6 |
| ≤22 | 8 (80.0%) |
| >22 | 2 (20.0%) |
| CRP (mg/l) | 21.5 ± 8.2 |
| Normal | 0 (0.0%) |
| Increased | 10 (100.0%) |
| D-dimer (ng/ml) | 525.4 ± 175.7 |
| Normal | 0 (0.0%) |
| Increased | 10 (100.0%) |

Clinical trials were conducted in a Smolensk clinic, Russia, in accordance with the Clinical Trial Protocol. The trials used identical protocols for all the tests for all patients.

Basic objective: to evaluate the efficacy of IV APR in COVID-19 patients hospitalized with clinical status 4 using the following parameters:

Time to elimination of SARS-CoV-2 virus to Day 10;

Time to normalize CRP to Day 10;

Time to normalize D-dimer to Day 10.

Additional objectives: same as in Example 1.

Study Design:

All 10 patients received APR intravenously by drop infusion (slowly for 15-20 minutes) 1,000,000 KIU once a day for 3 days (Table 9).

TABLE 9

Daily doses of the components of the combination agent received by patients treated from COVID-19 with aprotinin (APR)

| Patient | Age, years | Body height, cm | Body mass, kg | Body mass index, kg/m$^2$ | APR dose (KIU), once a day |
|---|---|---|---|---|---|
| 01 | 56 | 173 | 81.4 | 27.20 | 1 000 000 |
| 02 | 55 | 166 | 72.5 | 26.31 | 1 000 000 |
| 03 | 50 | 169 | 73.6 | 25.77 | 1 000 000 |

TABLE 9-continued

Daily doses of the components of the combination agent received by patients treated from COVID-19 with aprotinin (APR)

| Patient | Age, years | Body height, cm | Body mass, kg | Body mass index, kg/m$^2$ | APR dose (KIU), once a day |
|---|---|---|---|---|---|
| 04 | 24 | 160 | 72.1 | 28.16 | 0 |
| 05 | 43 | 176 | 78.7 | 25.41 | 0 |
| 06 | 31 | 170 | 75.5 | 26.12 | 0 |
| 07 | 41 | 168 | 65.2 | 23.10 | 0 |
| 08 | 48 | 179 | 73.5 | 22.94 | 0 |
| 09 | 49 | 169 | 79.3 | 27.77 | 0 |
| 10 | 60 | 165 | 71.4 | 26.23 | 0 |

Depending on the patients' condition and concomitant to COVID-19 diseases they received respective concomitant therapy (Table 10).

TABLE 10

Concomitant therapeutics used to treat patients hospitalized with COVID-19 and clinical status 4 with aprotinin (APR)

| Drug | X[a] | %[b] | Y[c] |
|---|---|---|---|
| Paracetamol | 10 | (100.0%) | 10 |
| Azithromycin | 9 | (90.0%) | 9 |
| Levofloxacin | 1 | (10.0%) | 1 |
| Enoxaparin | 10 | (100.0%) | 10 |
| Hydroxychloroquine | 9 | (90.0%) | 9 |
| Ringer's solution | 1 | (10.0%) | 1 |
| Lopinavir + Ritonavir | 1 | (10.0%) | 1 |
| Ritonavir | 1 | (10.0%) | 1 |

The cure rates of patients hospitalized with COVID-19, clinical status 4, who were treated with aprotinin are presented in Table 1.

EXAMPLE 4. KITS OF DRUGS FOR THE COMBINATION THERAPY OF CORONAVIRUS DISEASE

Kits of drugs for the combination therapy of coronavirus disease are made up of finished drugs in the required therapeutically effective amount and ratio (Table 2), which are placed in a package that protects drugs from external factors and contains instructions for use. APR lyophilizates are used as APR containing finished medicinal products: APROTEX® (aprotinin), INGITRIL® (aprotinin), CONTRYKAL® (aprotinin), KONTRISEL® (aprotinin); solutions for injections and infusions: TRASILOL® (aprotinin), INGIPROL® (aprotinin), APROTIMBIN® (aprotinin), GORDOX® (aprotinin), CONTRIVEN® (aprotinin), TRASCOLAN® (aprotinin); or aerosol for inhalation—AERUS® (aprotinin); and their analogues. AVIGAN® (favipiravir), AVIFAVIR® (favipiravir), FAVILAVIR® (favipiravir), CORONAVIR® (favipiravir), and FABIFLU® (favipiravir), and their analogues, are used as FVP-containing finished medicinal products. [https://myhep.com.ua/preparaty/oncology/fabiflu/].

TABLE 11

Compositions of packages of an anti-coronavirus agent, including APR and FVP or RMD, for the 1st course of treatment of the 1st patient.

| | |
|---|---|
| Kit 1: | 1. APR containing ready-made medicinal products: 50 ampoules of solution for injection, 100,000 KIE/ampoule 10 ml or 10 bottles of solution for injection, 500,000 KIE/bottle of 50 ml or 25 bottles of lyophilisate, 200,000 KIE/bottle for preparation of 50 ml of solution for injection or 10 vials of lyophilisate, 500,000 KIE/vial for preparation of 50 ml solution for injections. |

TABLE 11-continued

| Compositions of packages of an anti-coronavirus agent, including APR and FVP or RMD, for the 1st course of treatment of the 1st patient. | |
|---|---|
| | 2. FVP containing finished medicinal products (tablets containing 200 mg of FVP): 7 blisters of 10 tablets each or 1 bottle - 70 tablets |
| Kit 2: | 1. APR containing ready-made medicinal products: 50 ampoules of solution for injection, 100,000 KIE/ampoule 10 ml or 10 bottles of solution for injection, 500,000 KIE/bottle of 50 ml or 25 bottles of lyophilisate, 200,000 KIE/bottle for preparation of 50 ml of solution for injection or 10 vials of lyophilisate, 500,000 KIE/vial for preparation of 50 ml solution for injections. 2. FVP containing ready-made medicinal products (tablets containing 200 mg of FVP): 10 blisters of 10 tablets each or 1 bottle - 92 tablets. |
| Kit 3: | 1. APR containing ready-made medicinal products: 50 ampoules of solution for injection, 100,000 KIE/ampoule 10 ml or 10 bottles of solution for injection, 500,000 KIE/bottle of 50 ml or 25 bottles of lyophilisate, 200,000 KIE/bottle for preparation of 50 ml of solution for injection or 10 vials of lyophilisate, 500,000 KIE/vial for preparation of 50 ml solution for injections. 2. FVP containing finished medicinal products (tablets containing 200 mg of FVP): 12 blisters of 10 tablets each or 1 bottle - 114 tablets. |
| Kit 4: | 1. APR containing ready-made medicinal products: 50 ampoules of solution for injection, 100,000 KIE/ampoule of 10 ml or 10 bottles of solution for injection, 500,000 KIE/bottle of 50 ml or 25 bottles of lyophilisate, 200,000 KIE/bottle for preparation of 50 ml of solution for injection or 10 vials of lyophilisate, 500,000 KIE/vial for preparation of 50 ml solution for injection. 2. RMD VEKLURY ® (remdesivir) for injection 7 vials of 100 mg of sterile, preservative-free lyophilized powder of RMD in each single-use vial, which is dissolved and diluted in 19 ml of sterile water for injection before use and additionally diluted with saline in an infusion bag. |
| Kit 5: | 1. APR containing ready-made medicinal products: 50 ampoules of solution for injection, 100,000 KIE/ampoule 10 ml or 10 vials of solution for injections, 500,000 KIE/vial 50 ml or 25 vials of lyophilisate, 200,000 KIE/vial for preparation of 50 ml solution for injections or 10 vials of lyophilisate, 500,000 vials/vial for preparation of 50 ml solution for injections. 2. RMD VEKLURY ® (remdesivir) for injection 12 vials of 100 mg of sterile, preservative-free lyophilized powder of RMD in each single-use vial, which is dissolved and diluted in 19 ml of sterile water for injection before use and additionally diluted with saline in an infusion bag. |

The clinical study included 3 groups of patients hospitalized with COVID, including: 10 patients who received intravenous APR+oral FP (Group 1), 11 patients received oral FP (Group 2), 10 patients received intravenous APR (Group 3). Patients received a combined agent from kits No. 1-No. 3. Patient demographics and other baseline characteristics are presented in the tables. The efficacy of the combined treatment of hospitalized patients with COVID-19 and clinical status 4 with the anti-coronavirus agent of this invention and its constituents is shown in Table 1.

INDUSTRIAL APPLICABILITY

The invention can be used in medicine and veterinary medicine.

The invention claimed is:

1. A pharmaceutical combination for treatment of COVID-19 (SARS-CoV-2) comprising, in a therapeutically effective amount and ratio, aprotinin (APR) and favipiravir (FVP), for simultaneous, separate, or sequential administration.

2. The combination according to claim 1, wherein the aprotinin is comprised in a separate pharmaceutical composition containing one or more pharmaceutically acceptable excipients, diluents, or carriers.

3. The combination according to claim 1, wherein the favipiravir is comprised in a separate pharmaceutical composition containing one or more pharmaceutically acceptable excipients, diluents, or carriers.

4. The pharmaceutical combination according to claim 1, wherein the aprotinin is formulated for parenteral administration or inhalation, and the favipiravir is formulated for oral administration.

5. The pharmaceutical combination according to claim 1, wherein the therapeutically effective amount of aprotinin is between 500,000 KIU and 1,000,000 KIU.

6. The pharmaceutical combination according to claim 1, wherein the aprotinin is in the form of a lyophilizate, a solution for injection, or a dosed aerosol for inhalation.

7. A method of treating COVID-19 (SARS-CoV-2) comprising administering to a human subject in need thereof a therapeutically effective combination of (a) aprotinin (APR) and (b) favipiravir (FVP), in a therapeutically effective amount and ratio.

8. The method according to claim 7, wherein the favipiravir is comprised in a separate pharmaceutical composition containing one or more pharmaceutically acceptable excipients, diluents, or carriers.

9. The method according to claim 7, wherein the aprotinin is comprised in a separate pharmaceutical composition containing one or more pharmaceutically acceptable excipients, diluents, or carriers.

10. The method according to claim 7, wherein the aprotinin is administered intravenously and the favipiravir is administered orally.

11. The method according to claim 7, wherein the aprotinin is administered at a dose of 500,000 KIU to 1,000,000 KIU once per day for up to 5 days.

12. The method according to claim 7, wherein the favipiravir is administered according to a regimen comprising a loading dose on Day 1 followed by a maintenance dose on Days 2 to 10.

13. The method according to claim 12, wherein the loading dose comprises a dose of 1200 mg to 2000 mg and the maintenance dose comprises 400 mg to 800 mg.

14. The method according to claim 7, wherein the therapeutically effective combination provides a synergistic reduction in C-reactive protein (CRP) concentration or D-dimer concentration in the subject.

15. A pharmaceutical kit for combination therapy of coronavirus disease COVID-19 (SARS-CoV-2) comprising:

A. aprotinin (APR) in a therapeutically effective amount in the form of a finished medicinal product or in the form of finished product components suitable for its administration;

B. favipiravir (FVP) in a therapeutically effective amount in the form of a finished medicinal product, with a therapeutically effective ratio of APR and FVP, placed in a package that protects drugs from external factors, and C. instructions for use.

* * * * *